United States Patent [19]

Ueda et al.

[11] Patent Number: 5,045,553

[45] Date of Patent: Sep. 3, 1991

[54] PHARMACEUTICAL COMPOSITION FOR PERCUTANEOUS DRUG ABSORPTION AND PERCUTANEOUS DRUG ABSORPTION PROMOTER

[75] Inventors: Yoshio Ueda, Kobe; Takehisa Hata, Muko; Rinta Ibuki, Ashiya; Kazutake Kado, Toyonaka; Hiroshi Ishikuro, Ikeda, all of Japan

[73] Assignee: Fujisawa Pharmaceutical Company, Ltd., Osaka, Japan

[21] Appl. No.: 208,071

[22] Filed: Jun. 17, 1988

[30] Foreign Application Priority Data

Jun. 24, 1987 [JP] Japan .................. 62-157234
Sep. 10, 1987 [JP] Japan .................. 62-227113

[51] Int. Cl.$^5$ .............................. A61K 31/44
[52] U.S. Cl. ........................ 514/344; 424/449; 514/947
[58] Field of Search ........... 514/344, 447; 424/444

[56] References Cited

U.S. PATENT DOCUMENTS 4,338,322 7/1982 Sato .................. 424/266
4,379,454 4/1983 Campbell et al. ......... 604/897
4,460,372 7/1984 Campbell et al. ......... 604/897

FOREIGN PATENT DOCUMENTS 0185283 6/1984 European Pat. Off. .

OTHER PUBLICATIONS

Chemical Abstracts 105: 158835x, 1986, (Kinoshita et al.).

E. R. Cooper, "Increased Skin Permeability for Lipophilic Molecules," J. Pharm. Sci., vol. 73, No. 8, pp. 1153–1156 (1984).

E. R. Cooper et al., "Effect of Fatty Acids and Alcohols on the Penetration of Acyclovir Across Human Skin in Vitro", J. Pharm. Sci., vol. 74, No. 6, pp. 688–689 (1985).

*Primary Examiner*—Leonard Schenkman
*Attorney, Agent, or Firm*—Oblon, Spivak, McClelland, Maier & Neustadt

[57] ABSTRACT

The present invention relates to a pharmaceutical composition for percutaneous drug absorption which comprises 5-isopropyl 3-methyl 2-cyano-6-methyl-4-(3-nitrophenyl)-1,4-dihydropyridine-3,5-dicarboxylate, and ethanol and/or an unsaturated higher fatty acid and to a composition of matter which comprises ethanol and/or an unsaturated higher fatty acid and is capable of promoting percutaneous absorption of said dihydropyridine compound.

8 Claims, 2 Drawing Sheets

PHARMACEUTICAL COMPOSITION FOR PERCUTANEOUS DRUG ABSORPTION AND PERCUTANEOUS DRUG ABSORPTION PROMOTER

The present invention relates to a pharmaceutical composition which comprises the above-mentioned dihydropyridine compound as an active ingredient, and ethanol and/or an unsaturated higher fatty acid as a substance that promotes percutaneous absorption of said compound The invention further relates to a percutaneous absorption promoter which comprises ethanol and/or an unsaturated higher fatty acid which is capable of promoting percutaneous absorption of the above-mentioned dihydropyridine compound.

The dihydropyridine compound which is the active ingredient and the percutaneous absorption of which is to be promoted in accordance with the invention has the following chemical formula:

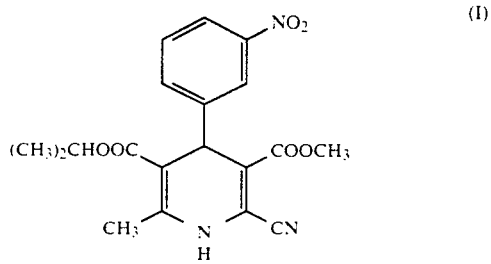

The dihydropyridine compound (I) has vasodilating activity and is useful in the treatment of coronary angiopathy, such as angina pectoris or myocardial infarction, or hypertension.

This dihydropyridine compound includes two optically active isomers, namely dextrorotatory and levorotatory ones, resulting from the presence of an asymmetric carbon atom in the 4-position of the dihydropyridine ring and mixtures thereof. In particular, the optically inactive racemic mixture is known by the generic name "nilvadipine".

The dihydropyridine compound (I) to be used as the chief ingredient in accordance with the invention is sparingly soluble in water and, as such, can be absorbed percutaneously only to a slight extent. It has been thought difficult to attain an effective drug concentration in the blood by percutaneous administration. On the other hand, the conventional oral preparations are still more or less unsatisfactory from the sustained action viewpoint although they are satisfactory in promptness in action. Accordingly, a preparation for percutaneous administration which can release the drug sustainedly has been waited for.

As a result of their intensive investigations made in an attempt to overcome the above problems, the inventors of this invention found that ethanol and/or an unsaturated higher fatty acid can markedly promote the percutaneous absorption of the dihydropyridine compound (I). This finding has now led to completion of this invention.

Accordingly, one object of this invention is to provide a pharmaceutical composition for percutaneous drug absorption which comprises the dihydropyridine compound (I) as the chief active ingredient, and ethanol and/or an unsaturated higher fatty acid as a percutaneous absorption promoter and which may contain, as optional component(s), (an)other percutaneous absorption promoter(s) for increasing the absorbability of said compound further Another object of this invention is to provide a percutaneous drug absorption promoter which comprises ethanol and/or an unsaturated higher fatty acid and is capable of markedly promoting the percutaneous absorption of the dihydropyridine compound (I).

In the accompanying drawings.

Figure 5:
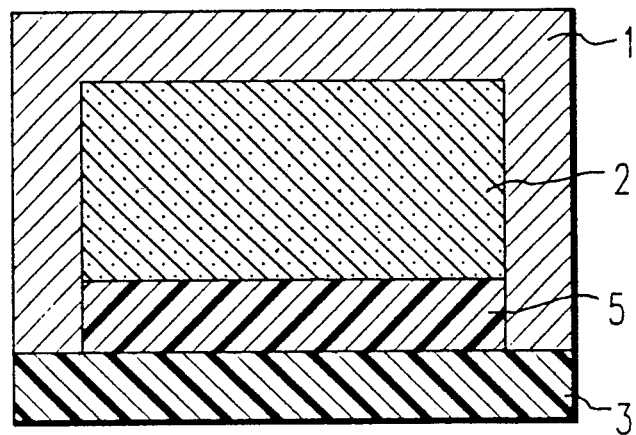
Figure 6:
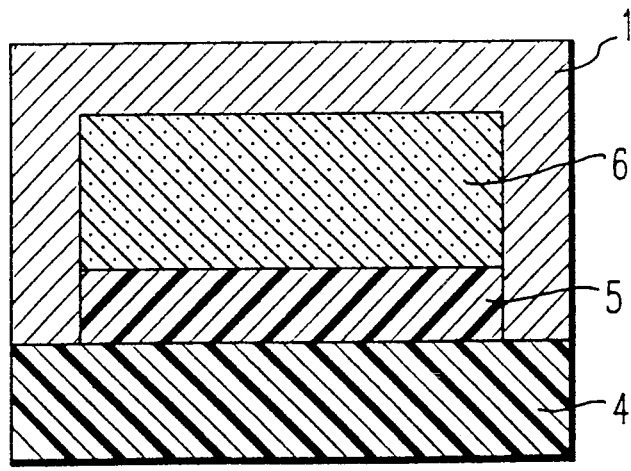

FIG. 5 is a sectional view schematically illustrating a patch preparation, wherein the drug migration is controlled through membrane permeation and wherein said preparation is further provided with an adhesive layer; and FIG. 6 is a sectional view schematically illustrating a patch preparation, wherein the adhesive layer contains the chief ingredient and wherein the release of absorption promoter from the sustained release matrix, which is free of the chief ingredient, is controlled through membrane permeation.

In the figures, the reference numeral (1) indicates a support member, (2) a drug-containing, sustained release matrix, (3) an adhesive layer, (4) a drug-containing adhesive layer, (5) an absorption promoter release-controlling membrane or film, and (6) a drug-free sustained release matrix.

The unsaturated higher fatty acid to be used as the percutaneous absorption promoter in the pharmaceutical composition for percutaneous drug absorption in accordance with the present invention includes straight-chain or branched-chain aliphatic carboxylic acids containing 10 to 26 carbon atoms and 1 to 5 unsaturated bond(s), for example palmitolic acid, oleic acid, ricinolic acid, linolic acid, linoleic acid and eleostearic acid. Preferred among them are straight-chain aliphatic carboxylic acids containing 14 to 22 carbon atms and 1 to 3 unsaturated bonds Particularly preferred is oleic acid.

As percutaneous absorption promoter(s) which is- (are) other than ethanol or the unsaturated higher fatty acids and is(are) to be added as optional component(s) to the pharmaceutical composition for percutaneous drug absorption according to the invention, there may be mentioned, for example, fatty acid esters, such as diethyl sebacate and isopropyl myristate, phospholipids, such as lecithin, mono-, di- or triglycerides, other nonionic surfactants, sulfonic acid esters, pyrrolidone and derivatives thereof The pharmaceutical composition for percutaneous drug absorption according to the invention can be produced by a conventional method.

Thus, the base for use in preparing said pharmaceutical composition may be any base which is dermatocompatible or dermatologically acceptable and at the same time compatible with the dihydropyridine compound (I) and/or ethanol and/or an unsaturated higher fatty acid without unfavorably affecting the dissolution, diffusion and other behaviors of the chief ingredient in said pharmaceutical composition Such base includes, but is not limited to, water, room temperature-curable or thermosetting silicone polymers (e.g. silicone elastomers, etc.), hydrogels obtained from water-soluble macromolecules or hydrogelating agent [e.g. agar, gelatin, carrageenan, chitosan, agarose, konnyaku, polyvinyl alcohol, polyvinylpyrrolidone, poly(2-hydroxyethyl methacrylate), hydroxypropylmethylcellulose, carboxymethylcellulose, hydroxypropylcellulose (hydroxypropylcellulose-H, etc.), hydroxyethylcellulose, etc.], products of gelation of liquid paraffin, triglycerides and the like with lecithin, ethylcellulose or the like, and so forth.

When said pharmaceutical composition contains ethanol, water is preferably used as a base and it is preferable to add thereto a hydrogel or hydrogelating agent such as mentioned above or the like for gelation.

Said base may contain a hydrophilic solvent or a hydrophobic solvent as a release aid for the active ingredient. As such hydrophilic solvent, there may be mentioned, for example, polyhydric alcohols such as propylene glycol, polyethylene glycol (e.g polyethylene glycol 400, polyethylene glycol 4,000, etc.) and glycerin, and mixtures of these As said hydrophobic solvent, there may be mentioned medium-chain fatty acid glycerides such as Panacete and Miglyol, liquid paraffin, and mixtures of these, among others.

With said pharmaceutical composition, the rate of percutaneous absorption of the chief ingredient can be controlled, for example by dispersing the chief ingredient in an appropriate dermatocompatible sustained release matrix base so that the diffusion of the chief ingredient in the base can serve as a percutaneous absorption rate-determining factor. As such dermato-compatible base, there may be mentioned those dermato-compatible bases mentioned above. The rate of release of the chief ingredient from the base can be optionally controlled by adding any of the above-mentioned hydrophilic or hydrophobic solvents to said base as necessary.

The pharmaceutical composition for percutaneous drug absorption according to the invention can be administered in various dosage forms.

Figure 1:
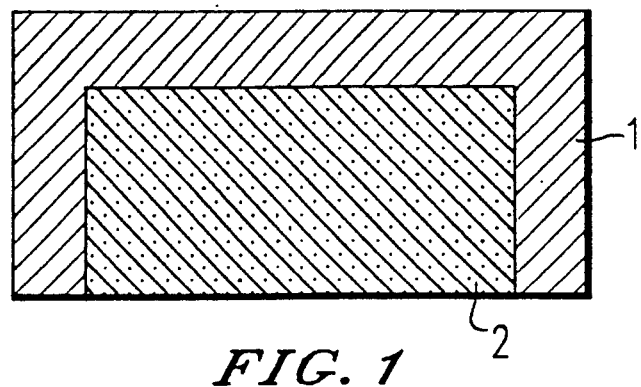
FIG. 1 is a sectional view schematically illustrating a patch preparation the drug release from which is controlled by means of a sustained release matrix.
Figure 2:
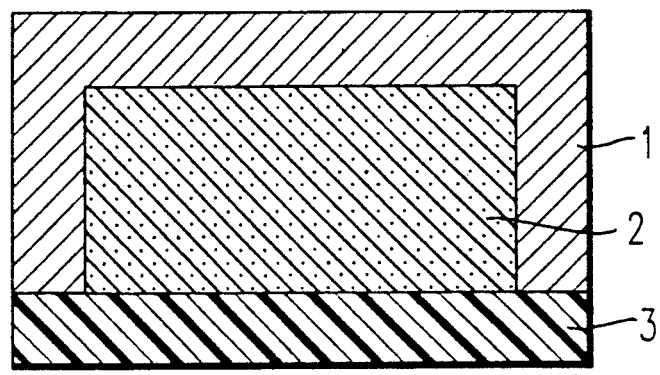
FIG. 2 is a sectional view schematically illustrating a patch preparation the drug release from which is controlled by means of a sustained release matrix and which is further provided with an adhesive layer.

When the pharmaceutical composition is to have the form of patches, said composition is spread over a support member (made of cloth or aluminum, for instance) (cf. FIG. 1) and, if necessary, an adhesive layer is provided (cf. FIG. 2).

Figure 3:
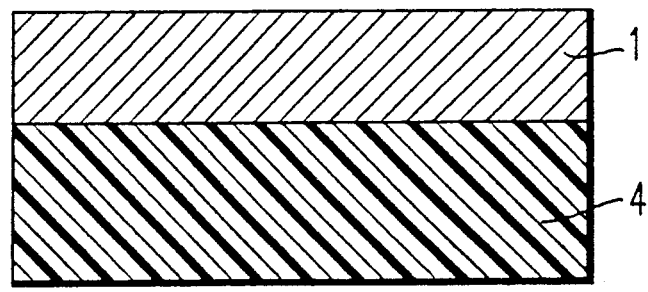
FIG. 3 is a sectional view schematically illustrating a tape preparation.

For producing adhesive tapes, the pharmaceutical composition according to the invention is mixed with an appropriate adhesive mass and the mixture is applied to an appropriate support member (cf. FIG. 3). In this case, the adhesive mass may be any adhesive mass usable in preparing ordinary adhesive tapes for medical use and can be selected depending on the desired rate of the drug release, for example from among silicone adhesives (Dow Corning's 355 Medical Adhesive, etc), rubber-based adhesives (Japan Synthetic Rubber's JSR0585, etc.), acrylic adhesives (Japan Acrylic Chemical's Primal N580S, Nippon Junyaku's ST811, etc.) and so forth.

The pharmaceutical composition for percutaneous drug absorption according to the invention may also be made up into ointments for ordinary use, such as Macrogol ointments, FAPG ointments, hydrophilic ointments, absorptive ointments, Carbopol gel ointments, etc. In this case, for providing sustained release property, controlling drug absorption and preventing adherence to clothes, it is also possible to fill the composition in an appropriate container and attach the container to the skin so that said composition can come into contact therewith or to coat a support member (as in the case of tape preparations) with said composition to a certain thickness and apply the whole to the skin so that said composition can come into contact therewith.

Figure 4:
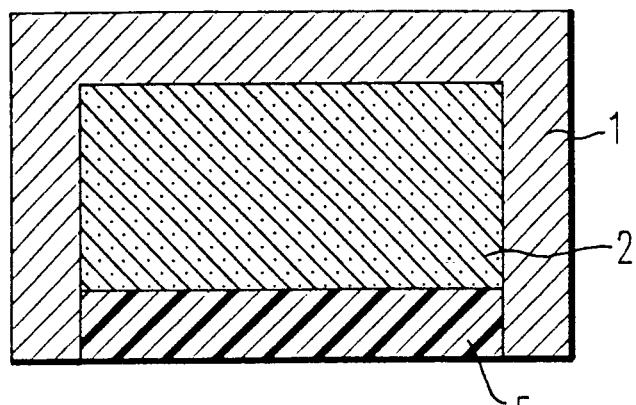
FIG. 4 is a sectional view schematically illustrating a patch preparation, wherein the drug migration is controlled through membrane permeation.

Furthermore, the pharmaceutical composition for percutaneous drug absorption according to the invention can be made up into patches, for example by spreading said composition over an appropriate support member (made of aluminum, for instance) and, if necessary, sealing with an absorption promoter release-controlling film such as an ethylene-vinyl acetate copolymer (EVA) film (cf. FIG. 4), and furthermore, if necessary, providing an adhesive layer (cf. FIG. 5). With these patches, drug absorption can ben controlled by interposing such absorption promoter release controlling film or membrane between said pharmaceutical composition or adhesive layer and the skin so that an effective blood concentration of the chief ingredient can be maintained for a prolonged period of time. The rate of drug absorption can be controlled as desired by adequately modifying the thickness of said absorption promoter release controlling film and/or the composition of the EVA film. Furthermore, the chief ingredient and/or the above-mentioned absorption promoter may be added to the adhesive layer as necessary so that the percutaneous absorbability can be increased and/or the absorption of the chief ingredient can be maintained.

In cases where the pharmaceutical composition for percutaneous drug absorption is made up into patches, it is not always necessary that the chief ingredient and absorption promoter be present in the same layer. Thus, for example, patches may be prepared by spreading a dermatocompatible sustained release matrix free of the chief ingredient over a support member, then sealing with an absorption promoter release controlling film and further providing thereon an adhesive layer containing the chief ingredient (cf. FIG. 6).

The pharmaceutical composition for percutaneous drug absorption according to the invention may be made up into any other dosage forms in which the chief ingredient can be absorbed percutaneously The above-mentioned dosage form examples are by no means limitative of the dosage forms employable When the pharmaceutical composition comprises the chief ingredient and ethanol, the content ratio between the chief ingredient and ethanol is not particularly limited. Preferably, however, the chief ingredient content should be 0.01–30% by weight, more preferably 0.1–20% by weight, and the ethanol content should be 10–95% by weight, more preferably 40–80% by weight, based on the total amount of this composition. When the pharmaceutical composition comprises the chief ingredient and an unsaturated higher fatty acid, the content ratio between the chief ingredient and the unsaturated higher fatty acid is not particularly limited. Preferably, however, the chief ingredient content should be 0.01–20% by weight, more preferably 0.1–10% by weight, and the content of said fatty acid should be 0.1–40% by weight, more preferably 0.5–20% by weight, based on the total amount of this composition. In cases where the pharmaceutical composition comprises the chief ingredient, ethanol and an unsaturated higher fatty acid, the content ratio among the chief ingredient, ethanol and the unsaturated higher fatty acid is not particularly limited, either. Preferably, however, their contents should preferably be 0.01-20% by weight, 5-95% by weight and 0.1-40% by weight, respectively, more preferably 0.1-10% by weight, 10-80% by weight and 1-30% by weight, respectively, based on the total amount of this composition.

In a most preferred embodiment of the present invention, the pharmaceutical composition for percutaneous drug absorption comprises the chief ingredient, ethanol and oleic acid and, if desired, may contain another percutaneous absorption promoter.

The pharmaceutical composition for percutaneous drug absorption according to the invention is preferably made up into patches such as mentioned above.

The following examples are further illustrative of the present invention but are by no means limitative of the scope thereof.

| Example 1 | |
|---|---|
| Nilvadipine | 5% by weight |
| Ethanol | 60% by weight |
| Water | 40% by weight |

Ethanol and water were added to nilvadipine and the mixture was stirred, whereby a suspension was obtained.

| Example 2 | |
|---|---|
| Nilvadipine | 5% by weight |
| Ethanol | 55.8% by weight |
| Water | 37.2% by weight |
| Hydroxypropylcellulose-H (HPC-H) | 2% by weight |

Nilvadipine was added to ethanol and the mixture was stirred. Water and HPC-H were, then, added to the mixture and the mixture was stirred, whereby a suspension gel was obtained.

| Example 3 | |
|---|---|
| Nilvadipine | 1% by weight |
| Ethanol | 58.2% by weight |
| Water | 38.8% by weight |
| HPC-H | 2% by weight |

A solution gel was obtained by proceeding in the same manner as in Example 2.

| Example 4 | |
|---|---|
| Nilvadipine | 5.0% by weight |
| Polyethylene glycol 400 (PEG 400) | 51.5% by weight |
| Polyethylene glycol 4,000 (PEG 4,000) | 38.5% by weight |
| Oleic acid | 5.0% by weight |

Nilvadipine was added to a mixture of polyethylene glycol 400 and polyethylene glycol 4,000 which had been melted by heating on a water bath at 65° C. After dissolution of nilvadipine, oleic acid was further added and, after dissolution of oleic acid, the temperature was lowered gradually while the mixture was stirred thoroughly until it became rigid. Thus was prepared a pharmaceutical composition for percutaneous drug absorption.

| Example 5 | |
|---|---|
| Nilvadipine | 10% by weight |
| Oleic acid | 20% by weight |
| ST811[1] | 70% by weight |
| Ethyl acetate | 300% by weight |

[1]Acrylic acid-butyl acrylate (3:97) copolymer]

Nilvadipine, oleic acid and ST811 were dissolved in ethyl acetate and the solution was applied to a release paper by means of a knife coater to a thickness after drying of 100 μm. After drying, a tape preparation was obtained.

| Example 6 | |
|---|---|
| Nilvadipine | 5% by weight |
| Oleic acid | 10% by weight |
| Ethanol | 49.8% by weight |
| Water | 33.2% by weight |
| HPC-H | 2% by weight |

Nilvadipine and oleic acid were added to ethanol and the mixture was stirred. Water and HPC-H were, then, added to the mixture and the mixture was stirred, whereby a suspension gel was obtained.

| Example 7 | |
|---|---|
| Nilvadipine | 1% by weight |
| Oleic acid | 10% by weight |
| Ethanol | 52.2% by weight |
| Water | 34.8% by weight |
| HPC-H | 2% by weight |

A solution gel was obtained by proceeding in the same manner as in Example 6.

| Example 8 | |
|---|---|
| 5-Isopropyl 3-methyl (−)-2-cyano-6-methyl-4-(3-nitrophenyl)-1,4-dihydro-pyridine-3,5-dicarboxylate | 5% by weight |
| Oleic acid | 10% by weight |
| Ethanol | 49.8% by weight |
| Water | 33.2% by weight |
| HPC-H | 2% by weight |

A solution gel was obtained by proceeding in the same manner as in Example 6.

Example 9

The suspension gel obtained in Example 6 was spread over a support member made of aluminum in an amount of 40.2 mg per square centimeter. The gel layer was covered with an EVA film (vinyl acetate content 14%, thickness 50 μm). After heat sealing, there was obtained a patch preparation.

Example 10

A patch preparation was produced by using the solution gel obtained in Example 8 and following the procedure of Example 9.

| Example 11 | |
|---|---|
| Nilvadipine | 5% by weight |
| Oleic acid | 25% by weight |
| Ethanol | 10% by weight |

| Example 11 | |
|---|---|
| PEG 400 | 31.5% by weight |
| PEG 4,000 | 28.5% by weight |

PEG 400 and PEG 4,000 were melted by heating at 65° C. on a water bath, nilvadipine was added to the melt for dissolution therein, oleic acid and ethanol were further admixed with the solution, and the temperature was lowered gradually while the mixture was stirred well until it became rigid. Thus was obtained a pharmaceutical composition.

Example 12

A patch preparation was produced by using the solution gel obtained in Example 7 and an EVA film (vinyl acetate content 14%, thickness 50 μm) and following the procedure of Example 9. In this example, however, the gel was spread over the aluminum support in an amount of 38.3 mg per square centimeter.

Example 13

A patch preparation like that obtained in Example 12 was produced by using a 30-μm-thick EVA film having a vinyl acetate content of 14%.

Example 14

A patch preparation was produced by further forming an acrylic adhesive layer on the EVA film of the patch preparation produced in Example 13. The adhesive layer was prepared from the following components:

| Nilvadipine | 10% by weight |
|---|---|
| Oleic acid | 20% by weight |
| ST811 | 70% by weight |
| Ethyl acetate | 300% by weight |

Nilvadipine, oleic acid and ST811 were dissolved in ethyl acetate. The adhesive mass thus obtained was applied to a release paper by means of a knife coater to a thickness after drying of 100 μm and the coat layer was dried.

| Example 15 | |
|---|---|
| Gel: | |
| Ethanol | 58.8% by weight |
| Water | 39.2% by weight |
| HPC-H | 2% by weight |

A gel was prepared by adding HPC-H to ethanol and water.

| Adhesive mass: | |
|---|---|
| Nilvadipine | 10% by weight |
| ST811 | 90% by weight |
| Ethyl acetate | 300% by weight |

Nilvadipine and ST811 were dissolved in ethyl acetate. The solution was spread over a release paper by means of a knife coater to a thickness after drying of 100 μm and the coat layer was dried.

The above gel was spread over an aluminum support in an amount of 34 mg of gel per square centimeter. The gel layer was covered with an EVA film (vinyl acetate content 14%, thickness 30 μm), which was heat-sealed. The EVA film was further coated with the adhesive mass prepared as described above. Thus was obtained a patch preparation.

| Example 16 | |
|---|---|
| Nilvadipine | 1% by weight |
| Oleic acid | 10% by weight |
| Ethanol | 52.2% by weight |
| PEG 400 | 5% by weight |
| Water | 29.8% by weight |
| HPC-H | 2% by weight |

Nilvadipine and oleic acid were dissolved in ethanol and PEG 400 with stirring. Water and HPC-H were added to the solution and the mixture was stirred, whereby a solution gel was obtained.

| Example 17 | |
|---|---|
| 5-Isopropyl 3-methyl (±)-2-cyano-6-methyl-4-(3-nitrophenyl)-1,4-dihydropyridine-3,5-dicarboxylate | 5% by weight |
| Oleic acid | 10% by weight |
| Ethanol | 49.8% by weight |
| PEG 400 | 5% by weight |
| Water | 28.2% by weight |
| HPC-H | 2% by weight |

A solution gel was obtained by proceeding in the same manner as in Example 16.

Example 18

The solution gel obtained in Example 16 was spread over an aluminum support in an amount of 38.3 mg per square centimeter. The gel layer was then covered with an EVA film (vinyl acetate content 14%, thickness 30 μm), followed by heat sealing. Thus was produced a patch preparation.

Example 19

A patch preparation was produced by using the solution gel obtained in Example 17 and following the treatment procedure of Example 18. The gel was applied to the aluminum support in an amount of 40.2 mg per square centimeter.

| Example 20 | |
|---|---|
| Nilvadipine | 1% by weight |
| Oleic acid | 8% by weight |
| Ethanol | 53.4% by weight |
| PEG 400 | 5% by weight |
| Water | 30.6% by weight |
| HPC-H | 2% by weight |

Nilvadipine and oleic acid were dissolved in ethanol and PEG 400 with stirring. After further addition of water and HPC-H to the solution, the mixture was stirred to give a solution gel.

| Example 21 | |
|---|---|
| 5-Isopropyl 3-methyl (±)-2-cyano-6-methyl-4-(3-nitrophenyl)-1,4-dihydropyridine-3,5-dicarboxylate | 5% by weight |
| Oleic acid | 8% by weight |

-continued

| Example 21 | |
|---|---|
| Ethanol | 51% by weight |
| PEG 400 | 5% by weight |
| Water | 29% by weight |
| HPC-H | 2% by weight |

A solution gel was obtained by proceeding in the same manner as in Example 20.

Example 22

The solution gel was obtained in Example 20 was spread over an aluminum support in an amount of 37.45 mg per square centimeter. The gel layer was covered with an EVA film (vinyl acetate content 14%, thickness 30 μm), followed by heat sealing. A patch preparation was thus produced.

Example 23

A patch preparation was produced by using the solution gel obtained in Example 21 and following the procedure of Example 22. In this example, however, the gel was applied to the aluminum support in an amount of 39.22 mg per square centimeter.

| Comparative Example 1 | |
|---|---|
| Nilvadipine | 5% by weight |
| Water | 100% by weight |

Water was added to nilvadipine and the mixture was stirred to give a suspension.

| Comparative Example 2 | |
|---|---|
| Nilvadipine | 5.0% by weight |
| PEG 400 | 54.3% by weight |
| PEG 4,000 | 40.7% by weight |

Nilvadipine was added to and dissolved in PEG 400 and PEG 4,000 which had been melted by heating at 65° C. on a water bath. While the temperature was lowered gradually, the mixture was stirred well until it became rigid.

| Comparative Example 3 | |
|---|---|
| Nilvadipine | 10 parts by weight |
| ST811 | 90 parts by weight |
| Ethyl acetate | 300 parts by weight |

Nilvadipine and ST811 were dissolved in ethyl acetate and the solution was spread over a release paper by means of a knife coater to a thickness after drying of 100 μm. After drying, a tape preparation was obtained.

The use of ethanol and/or an unsaturated higher fatty acid as a percutaneous drug absorption promoter in accordance with the invention results in marked improvement in percutaneous absorption of the chief ingredient. In particular, the combined use of ethanol and oleic acid results in very remarkable improvement in said chief ingredient absorption.

The following test results are illustrative of the effect producible with the percutaneous absorption promoter(s) and the pharmaceutical composition for percutaneous drug absorption according to the present invention.

[A] In vitro skin permeation test (1) Test method

The apparatus used was a horizontal membrane type diffusion cell. The full-thickness rat skin was used as the permeable membrane. Male SD rats weighing 200-250 g were used. They were deprived of hair in the abdominal part with an electric clipper and a depilatory cream on the day before testing.

The inside of the cell which had an effective diffusion area of 5 $cm^2$ was filled with physiological saline containing 2% of a surfactant [BO-20 (trademark); Nippon Chemicals], and the rat skin was mounted on the cell. Each sample was applied to the corneum side of the skin, the drug quantity in the receptor phase was determined at timed intervals, and the rate of drug penetration through the skin was calculated.

The amounts of the samples were 2 ml and 50 mg/5 $cm^2$ in the case of suspension and PEG contaning preparation, respectively.

The receptor phase was maintained at 37° C.

[A-1] Comparative test with suspensions

Test preparations
Suspension of Comparative Example 1
Suspension of Example 1
Test results

| Test preparation | Drug penetration rate in steady state μg/$cm^2$/hour |
|---|---|
| Comparative Example 1 | 0.034 |
| Example 1 | 2.11 |

[A-2] Comparative test with PEG-containing preparations

Test preparations
Preparation of Comparative Example 2
Preparation of Example 4
Test results

| | Drug penetration rate in steady state μg/$cm^2$/hour |
|---|---|
| Comparative Example 2 | 0.40 |
| Example 4 | 6.11 |

[A-3] Comparative test with tape preparations

Test preparations
Tape preparations of Comparative Example 3
Tape preparations of Example 5
Test results

| | Drug penetration rate in steady state μg/$cm^2$/hour |
|---|---|
| Comparative Example 3 | 0.080 |
| Example 5 | 2.055 |

[B] In vitro skin permeation test (2)

Test method
The same method as used in test [A] was used except that the sample was applied in an amount of 20 mg as ethanol per square centimeter.

Test preparations
Suspension gel of Example 2
Solution gel of Example 3
Suspension gel of Example 6
Solution gel of Example 7
Test results

| Test preparation | Drug penetration rate in steady state μg/$cm^2$/hour |
|---|---|
| Example | |
| 2 | 0.57 |
| 3 | 0.72 |
| 6 | 2.05 |

| 7 | 7.45 |
|---|---|

[C] In vivo percutaneous absorption test in rats

Male SD rats of 7 weeks of age were used in groups of three. Each test tape specimen (7 cm²) was applied to the abdominal part deprived of hair the day before testing, and the plasma nilvadipine level was determined by ECD gas chromatography.

[C-1] Comparative test with tape preparations

Test preparations
Tape preparations of Comparative Example 3
Tape preparation of Example 5
Test results

| | Plasma level (ng/ml) | |
|---|---|---|
| | at 1 hour | at 8 hour |
| Comparative Example 3 | 0.06 ± 0.06 | 0.15 ± 0.03 |
| Example 5 | 0.66 ± 0.05 | 2.05 ± 0.20 |

[C-2] Test with ethanol-and oleic acid-containing patch preparations

Test preparations
Patch of Example 9
Patch of Example 10
Test results

| Test preparation | Plasma level (ng/ml) | |
|---|---|---|
| | at 4 hour | at 6 hour |
| Example 9 | 2.62 | 3.02 |
| Example 10 | 3.08 | 6.97 |

[D] In vivo percutaneous absorption test in dogs

Test method

A test preparation specimen (50 cm²) was applied to the thoracic part of a beagle dog as deprived of hair 2 days before testing, and the plasma nilvadipine level was determined by ECD gas chromatography.

[D-1] Test with patches having an adhesive layer

Test preparations
Patch of Example 14
Patch of Example 15
Test results

| Test preparation | Plasma level (ng/ml) | | |
|---|---|---|---|
| | at 4 hour | at 8 hour | at 24 hours |
| Example 14 | 4.33 | 5.28 | 2.58 |
| Example 15 | 0.47 | 1.41 | 0.97 |

(Each group consisting of 3 dogs.)

[D-2] Test with patches

Test preparations
Patch of Example 13
Patch of Example 18
Patch of Example 19
Patch of Example 22
Patch of Example 23

| Test preparation | Test results | | |
|---|---|---|---|
| | Plasma level (ng/ml) | | |
| | at 4 hour | at 8 hour | at 24 hours |
| Example 13 | 1.02 | 2.77 | 1.31 |
| Example 18 | 0.55 | 1.70 | 1.53 |
| Example 19 | 2.65 | 7.54 | 5.13 |
| Example 22 | 0.81 | 2.55 | 1.87 |
| Example 23 | 3.45 | 7.90 | 5.46 |

(Each group consisting of 3 dogs.)

The results of the above in vitro skin permeation test and in vivo percutaneous absorption tests clearly indicate that ethanol and/or oleci acid can markedly promote the percutaneous absorption of the dihydropyridine compound (I) and that pharmaceutical compositions for percutaneous absorption of the dihydropyridine compound (I) which improve absorption of said compound very much can be obtained by causing such absorption promoters to be contained therein.

What is claimed is:

1. A pharmaceutical composition for percutaneous drug absorption which comprises as an active ingredient 5-isopropyl 3-methyl 2-cyano-6-methyl-4-(3-nitrophenyl)-1,4-dihydropyridine-3,5-dicarboxylate, ethanol and oleic acid, wherein the content of the active ingredient is 0.01-20% by weight, the content of the ethanol is 5-95% by weight and the content of the oleic acid is 0.1-40% by weight of the composition.

2. A pharmaceutical composition for percutaneous drug absorption as claimed in claim 1, wherein the 5-isopropyl 3-methyl 2-cyano-6-methyl-4-(3-nitrophenyl..)-1,4-dihydropyridine-3,5-dicarboxylate is a racemic compound.

3. A pharmaceutical composition for percutaneous drug absorption as claimed in claim 1, wherein the 5-isopropyl 3-methyl 2-cyano-6-methyl-6-methyl-4-(3-nitrophenyl)-1,4-dihydropyridine-3,5-dicarboxylate is a dextro-rotatory compound.

4. A pharmaceutical composition for percutaneous drug absorption as claimed in claim 1, said composition being formulated in the form of a patch.

5. A pharmaceutical composition for percutaneous drug absorption as claimed in claim 1, said composition being formulated in the form of a tape-form preparation.

6. A method of treating coronary angiopathy or hypertension in a subject in need of said treatment, which comprises administering an effective amount of the composition of claim 1.

7. A process for preparing a pharmaceutical composition for percutaneous drug absorption which comprises
   1) spreading a drug-free sustained release matrix containing ethanol or unsaturated higher fatty acid over a support,
   2) covering the said matrix with an absorption promoter release control membrane, and then
   3) coating the absorption promoter release control membrane with a base containing 5-isopropyl 3-methyl 2-cyano-6-methyl-4-(3-nitrophenyl)-1,4-dihydropyridine-3,5-dicarboxylate.

8. The process of claim 7, wherein the unsaturated higher fatty acid is oleic acid.

* * * * *